United States Patent
Hirata et al.

(10) Patent No.: US 12,207,997 B2
(45) Date of Patent: Jan. 28, 2025

(54) NONWOVEN FABRIC, USE OF SAME, AND METHOD FOR PRODUCING NONWOVEN FABRIC

(71) Applicant: Asahi Kasei Kabushiki Kaisha, Tokyo (JP)

(72) Inventors: Daiki Hirata, Tokyo (JP); Hidesato Shibata, Tokyo (JP); Nobuhiro Inokuma, Tokyo (JP); Eiji Shiota, Tokyo (JP)

(73) Assignee: Mitsui Chemicals Asahi Life Materials Co., Ltd., Tokyo (JP)

( * ) Notice: Subject to any disclaimer, the term of this patent is extended or adjusted under 35 U.S.C. 154(b) by 0 days.

(21) Appl. No.: 18/019,028

(22) PCT Filed: Jun. 30, 2022

(86) PCT No.: PCT/JP2022/026350
§ 371 (c)(1),
(2) Date: Jan. 31, 2023

(87) PCT Pub. No.: WO2023/277157
PCT Pub. Date: Jan. 5, 2023

(65) Prior Publication Data
US 2024/0115432 A1    Apr. 11, 2024

(30) Foreign Application Priority Data

Jun. 30, 2021    (JP) .................................. 2021-108700

(51) Int. Cl.
| | |
|---|---|
| *A61F 13/511* | (2006.01) |
| *A61F 13/15* | (2006.01) |
| *A61F 13/514* | (2006.01) |

(52) U.S. Cl.
CPC .... *A61F 13/5116* (2013.01); *A61F 13/51401* (2013.01); *A61F 2013/15959* (2013.01); *A61F 2013/51173* (2013.01); *A61F 2013/51452* (2013.01)

(58) Field of Classification Search
CPC ........ A61F 13/511; A61F 13/514; D01F 6/46; D04H 3/16; D04H 3/007
See application file for complete search history.

(56) References Cited

U.S. PATENT DOCUMENTS

| | | | |
|---|---|---|---|
| 3,454,519 A * | 7/1969 | Cervini ...................... D01F 6/06 | 524/219 |
| 4,526,919 A * | 7/1985 | Edwards .................. C08L 23/06 | 524/232 |
| 5,981,068 A | 11/1999 | Tsujiyama et al. | |
| 2003/0157859 A1 | 8/2003 | Ishikawa | |
| 2003/0181112 A1 | 9/2003 | Ishikawa et al. | |
| 2011/0024951 A1 * | 2/2011 | Kolb ........................ B32B 27/08 | 264/512 |
| 2014/0066873 A1 | 3/2014 | Kawakami et al. | |
| 2015/0233031 A1 | 8/2015 | Kunimoto et al. | |
| 2016/0017518 A1 * | 1/2016 | Lorenzo ................. D04H 3/007 | 428/401 |
| 2016/0251788 A1 * | 9/2016 | Huang ................... B32B 27/322 | 442/382 |
| 2018/0044828 A1 * | 2/2018 | Inokuma ................... B32B 5/26 | |
| 2018/0213852 A1 | 8/2018 | Matsubara et al. | |
| 2018/0256772 A1 | 9/2018 | Floter et al. | |
| 2019/0153626 A1 * | 5/2019 | Fujie ....................... C08L 23/12 | |
| 2019/0194826 A1 | 6/2019 | Hansen et al. | |
| 2021/0087715 A1 | 3/2021 | Sugiuchi et al. | |

FOREIGN PATENT DOCUMENTS

| | | | | |
|---|---|---|---|---|
| CN | 1297075 A | | 5/2001 | |
| CN | 103387701 A | | 11/2013 | |
| CN | 104662218 A | | 5/2015 | |
| CN | 109154117 A | | 1/2019 | |
| CN | 111742087 A | | 10/2020 | |
| EP | 1044719 | * | 10/2000 | ............. B01D 69/10 |
| EP | 1101854 A1 | | 5/2001 | |
| JP | H07-054214 A | | 2/1995 | |
| JP | H08-209533 A | | 8/1996 | |
| JP | 2001-226865 A | | 8/2001 | |
| JP | 2002-069820 A | | 3/2002 | |

(Continued)

OTHER PUBLICATIONS

International Search Report issued in corresponding International Patent Application No. PCT/JP2022/026350 dated Aug. 30, 2022.
Kohori et al., "Effect of the Blending of Low Stereo-regularity Component in High-Speed Melt Spinning of Polypropylene," Seikei-Kakou, 20 (11): 831-839 (2008) (see English abstract and Figure 5).
Chand et al., "Structure and properties of polypropylene fibers during thermal bonding," Thermochimica Acta, 367-368, 155-160 (2001).
Written Opinion issued in corresponding International Patent Application No. PCT/JP2022/026350 dated Aug. 30, 2022.
International Preliminary Report on Patentability issued in corresponding International Patent Application No. PCT/JP2022/026350 dated Dec. 14, 2023.

*Primary Examiner* — Michele Kidwell
(74) *Attorney, Agent, or Firm* — Morgan, Lewis & Bockius LLP

(57) ABSTRACT

The present invention provides: a nonwoven fabric which gives a sufficiently soft touch when touched by a human hand, while being suppressed in slipperiness between nonwoven fabrics during the production process of a product such as a sanitary material; and a method for producing a nonwoven fabric. One embodiment of the present invention provides a nonwoven fabric which is formed of fibers containing a thermoplastic resin, wherein: the average single fiber fineness of the fibers is 0.7 dtex to 4.0 dtex; the fibers contain 0.01% by mass to 1.5% by mass of a fatty acid amide relative to the total mass of the fibers; and the coverage of the surfaces of the fibers by the fatty acid amide is from 20% to 90%.

11 Claims, No Drawings

(56) References Cited

FOREIGN PATENT DOCUMENTS

| | | |
|---|---|---|
| JP | 2004-156180 A | 6/2004 |
| JP | 2006-152482 A | 6/2006 |
| JP | 2010-168713 A | 8/2010 |
| JP | 2017-179658 A | 10/2017 |
| JP | 2018-119247 A | 8/2018 |
| JP | 2018-145536 A | 9/2018 |
| JP | 2019-196576 A | 11/2019 |
| JP | 2021-066980 A | 4/2021 |
| WO | 2012/153802 A1 | 11/2012 |
| WO | 2017/006972 A1 | 1/2017 |
| WO | 2020/067516 A1 | 4/2020 |

* cited by examiner

NONWOVEN FABRIC, USE OF SAME, AND METHOD FOR PRODUCING NONWOVEN FABRIC

FIELD

The present invention relates to a nonwoven fabric and an application thereof and a method for manufacturing a nonwoven fabric.

BACKGROUND

In recent years, higher performance has been required for absorbent articles such as sanitary materials, typified by disposable diapers, sanitary napkins, and incontinence pads. Particularly, softer sheets have been in demand for disposable diapers, such as the topsheet that comes into contact with the skin, the backsheet that needs to be comfortable to the touch, and the gathers portion which easily irritates the skin.

For example, the softness of a sanitary material sheet is particularly expressed by the flexibility and smoothness of the sheet. By satisfying these two factors of softness, a soft texture can be felt for the sanitary material sheet.

As a nonwoven fabric suitable for absorbent articles, PTL 1 below discloses a spunbonded nonwoven fabric comprised of a polyolefin resin containing a fatty acid amide as a lubricant.

CITATION LIST

Patent Literature

[PTL 1] Japanese Unexamined Patent Publication (Kokai) No. 2002-69820

SUMMARY

Technical Problem

However, in the spunbonded nonwoven fabric described in PTL 1, the lubricant migrates to the fiber surface, leading to the problem of a layered product (for example, a sanitary material) comprising the nonwoven fabric slipping and collapsing in a packing step of the product.

In view of the above problem, an object of an aspect of the present invention is to provide a nonwoven fabric capable of imparting a sense of sufficient softness when touched by human hands while suppressing slipperiness between nonwoven fabrics in a manufacturing process of products such as a sanitary material comprising the nonwoven fabric, an application thereof, and a manufacturing method for the nonwoven fabric.

Solution to Problem

The present invention encompasses the following aspects.
[1] A nonwoven fabric comprised of fibers comprising a thermoplastic resin, wherein an average single yarn fineness of the fibers is 0.7 dtex or more and 4.0 dtex or less, the fibers contain a fatty acid amide in an amount of 0.01% by mass or greater and 1.5% by mass or less with respect to a total fiber mass, and a fatty acid amide coverage on a surface of the fibers is 20% or greater and 90% or less.
[2] The nonwoven fabric according to the above Aspect 1, wherein the fibers contain a fatty acid amide in an amount of 0.6% by mass or less with respect to the total fiber mass.
[3] The nonwoven fabric according to the above Aspect 1 or 2, wherein the fibers contain a fatty acid amide in an amount of 0.1% by mass or greater with respect to the total fiber mass.
[4] The nonwoven fabric according to any of the above Aspects 1 to 3, wherein the thermoplastic resin is a polyolefin and a birefringence $\Delta n$ of the fibers is 0.015 or greater and 0.029 or less.
[5] The nonwoven fabric according to any of the above Aspects 1 to 4, wherein a fatty acid portion of the fatty acid amide has 22 carbon atoms or less.
[6] The nonwoven fabric according to any of the above Aspects 1 to 5, wherein the fatty acid amide is erucamide.
[7] The nonwoven fabric according to any of the above Aspects 1 to 6, wherein the thermoplastic resin contains 70% by mass or greater and 99% by mass or less of a high-melting-point thermoplastic resin having a melting point above a predetermined melting point and contains 1% by mass or greater and 30% by mass or less of a low-melting-point thermoplastic resin having a melting point below or equal to the predetermined melting point.
[8] The nonwoven fabric according to any of the above Aspects 1 to 7 which is a filament nonwoven fabric.
[9] An absorbent article comprising the nonwoven fabric according to any of the above Aspects 1 to 8.
[10] The absorbent article according to Aspect 9 which is a disposable diaper, a sanitary napkin, or an incontinence pad.
[11] A manufacturing method for the nonwoven fabric according to any of the above Aspects 1 to 8, wherein the method is a spunbond method comprising a spinning step, a cooling step, a collection step, and a bonding step,
a discharge rate in the spinning step is 4 m/min or more and 8 m/min or less, and
a cold air speed in the cooling step is 0.5 m/s or more and 1.5 m/s or less.
[12] The manufacturing method for a nonwoven fabric according to the above Aspect 11, wherein the fatty acid amide is erucamide.

Advantageous Effects of Invention

The nonwoven fabric according to an aspect of the present invention is capable of imparting a sense of sufficient softness when touched by human hands while suppressing slipperiness between nonwoven fabrics in a manufacturing process of products such as sanitary materials comprising the nonwoven fabric.

DESCRIPTION OF EMBODIMENTS

Hereinafter, embodiments (herein also referred to as the present embodiment) exemplifying the present invention will be described in detail. However, the present invention is not limited to these embodiments.

The present inventors, as a result of intensive studies to achieve the above object, have discovered that in a nonwoven fabric comprised of fibers comprising a thermoplastic resin, by having a specific average single yarn fineness for the fibers, having a specific content of a fatty acid amide in the fibers, and controlling the fatty acid amide coverage on the fiber surface within a specific range, a sufficient softness can be obtained while suppressing slipperiness between nonwoven fabrics.

<Nonwoven Fabric>

In one aspect of the present invention, a nonwoven fabric comprised of fibers comprising a thermoplastic resin, wherein an average single yarn fineness of the fibers is 0.7 dtex or more and 4.0 dtex or less, the fibers contain a fatty acid amide in an amount of 0.01% by mass or greater and 1.5% by mass or less with respect to a total fiber mass, and a fatty acid amide coverage on a surface of the fibers is 20% or greater and 90% or less, is provided.

The nonwoven fabric of the present embodiment may be a filament nonwoven fabric manufactured by a spunbond method or a staple nonwoven fabric manufactured by a curd method or a wetstock sheet-making method. However, from the viewpoints of strength, productivity, and reduction of skin irritation, a filament nonwoven fabric is preferable. As described herein, a filament nonwoven fabric means a nonwoven fabric defined in JIS-L-0222. The fiber length of the filament may be, for example, 55 mm or more.

The nonwoven fabric of the present embodiment is composed of fibers comprising a thermoplastic resin. Examples of the thermoplastic resin include polyolefins such as polyethylene, polypropylene, and copolymers of ethylene and/or propylene and other olefins; and polyesters such as polyethylene terephthalate and polylactic acid. The thermoplastic resin may be manufactured from petroleum as a raw material, or may be manufactured from a biomass raw material. The polypropylene may be a polymer synthesized with a general Ziegler-Natta catalyst, or may be a polymer synthesized with a single-site active catalyst typified by a metallocene. Examples of the other olefins include olefins each having 4 to 10 carbon atoms, specifically 1-butene, 1-pentene, 1-hexene, 4-methyl-1-pentene, and 1-octene. These other olefins may be used alone or in combinations of two or more. From the viewpoint of obtaining excellent dimensional stability during production of products such as sanitary materials, using polypropylene-based fibers, which are fibers composed of a polypropylene homopolymer and/or a polypropylene copolymer, is preferable.

The MFR (melt mass-flow rate) of the thermoplastic resin is preferably 5 g/10 min or more and 150 g/10 min or less, more preferably 5 g/10 min or more and 100 g/10 min or less, even more preferably 10 g/10 min or more and 85 g/10 min or less, particularly preferably 15 g/10 min or more and 70 g/10 min or less, and most preferably 20 g/10 min or more and 65 g/10 min or less. The MFR is measured and determined according to Table 1 of JIS-K7210, "Plastics—Determination of the melt mass-flow rate (MFR) and melt volume-flow rate (MVR) of thermoplastics", at a test temperature of 230° C. and a test load of 2.16 kg.

The thermoplastic resin constituting the fibers may be composed of two or more resins having different melting points. In one aspect, the thermoplastic resin contains a high-melting-point thermoplastic resin having a melting point above a predetermined melting point and a low-melting-point thermoplastic resin having a melting point below or equal to the predetermined melting point. The predetermined melting point is set as desired. Note that, a melting point in the present disclosure is a temperature corresponding to the maximum value of an endothermic peak measured from 30° C. to 300° C. at a temperature elevation rate of 10° C./min using a differential scanning calorimeter (DSC). Preferably, the content percentage of the high-melting-point thermoplastic resin is 70% by mass or greater and 99% by mass or less, and the content percentage of the low-melting-point thermoplastic resin is 1% by mass or greater and 30% by mass or less, with respect to the total thermoplastic resin mass of 100% by mass. More preferably, the content percentage of the high-melting-point thermoplastic resin is 80% by mass or greater and 97% by mass or less, and the content percentage of the low-melting-point thermoplastic resin is 3% by mass or greater and 20% by mass or less. When the content percentage of the low-melting-point thermoplastic resin is within the above range, the manufacture of a soft nonwoven fabric having satisfactory strength and bending flexibility is easy. The high-melting-point thermoplastic resin and the low-melting-point thermoplastic resin may each be composed of one or more resins. Each resin is classified as a high-melting-point thermoplastic resin or a low-melting-point thermoplastic resin depending on whether the melting point of the resin is above the predetermined melting point or not.

The difference between the melting point of the high-melting-point thermoplastic resin (the lowest melting point in case of two or more resins) and the melting point of the low-melting-point thermoplastic resin (the highest melting point in case of two or more resins), from the viewpoint of controlling crystallinity (more specifically, lowering crystallinity) of the fibers to inhibit migration of the fatty acid amide to the fiber surface, is preferably 10° C. or higher, 20° C. or higher, or 30° C. or higher, and is preferably 200° C. or lower, 180° C. or lower, or 160° C. or lower.

In one aspect, the above predetermined melting point may be set within the range of 80° C. or higher and 200° C. or lower, and may be set to, for example, 80° C., 85° C., 90° C., 95° C., 100° C., 105° C., 110° C., 115° C., 120° C., 130° C., 140° C., 150° C., 160° C., 170° C., 180° C., 190° C., or 200° C.

The melting point of the high-melting-point thermoplastic resin (each melting point in case of two or more resins) is preferably higher than 80° C., 90° C. or higher, or 100° C. or higher, and is preferably 300° C. or lower, 280° C. or lower, or 260° C. or lower.

The melting point of the low-melting-point thermoplastic resin (each melting point in case of two or more resins) is preferably 40° C. or higher, 50° C. or higher, or 60° C. or higher, and is preferably 200° C. or lower, 180° C. or lower, or 160° C. or lower.

Examples of the high-melting-point thermoplastic resin include resins such as polyethylene, polypropylene, and copolymers of these monomers and other olefins described above. The low-melting-point thermoplastic resin is preferably a resin having a melting point below that of the high-melting-point thermoplastic resin used by 10° C. or more. The low-melting-point thermoplastic resin may be a random copolymer, an alternating copolymer, a block copolymer, or a graft copolymer. From the viewpoint of compatibility, it is preferable that the high-melting-point thermoplastic fibers and the low-melting-point thermoplastic resin both be mainly composed of the same monomer. For example, when the high-melting-point thermoplastic fibers are polypropylene, the low-melting-point thermoplastic resin is preferably a polypropylene-based resin (specifically, a polypropylene homopolymer or copolymer). Further, the low-melting-point thermoplastic resin is not particularly limited, and may be a plastomer or an elastomer.

The MFR of the high-melting-point thermoplastic resin is preferably 5 g/10 min or more and 100 g/10 min or less, more preferably 10 g/10 min or more and 80 g/10 min or less, even more preferably 20 g/10 min or more and 70 g/10 min or less, and particularly preferably 30 g/10 min or more and 60 g/10 min or less. It is preferably that the MFR be 5 g/10 min or more and 100 g/10 min or less, particularly 10 g/10 min or more and 100 g/10 min or less, from the viewpoint of spinnability with very little yarn breakage.

The MFR of the low-melting-point thermoplastic resin is preferably 5 g/10 min or more and 80 g/10 min or less, more preferably 5 g/10 min or more and 70 g/10 min or less, even more preferably 10 g/10 min or more and 60 g/10 min or less, and particularly preferably 10 g/10 min or more and 40 g/10 min or less. When the MFR is 5 g/10 min or more and 80 g/10 min or less, spinnability is excellent with very little yarn breakage.

In one aspect, the average single yarn fineness of the fibers constituting the nonwoven fabric of the present embodiment is 0.7 dtex or more and 4.0 dtex or less, preferably 0.7 dtex or more and 3.0 dtex or less, and more preferably 0.7 dtex or more and 2.0 dtex or less. In one aspect, from the viewpoint of spinning stability, the average single yarn fineness is 0.7 dtex or more. In one aspect, from the viewpoint of imparting to the nonwoven fabric strength that is particularly advantageous (i.e., not excessively high) for sanitary materials, the average single yarn fineness is 4.0 dtex or less. Note that, as the average single yarn fineness of the fibers constituting the nonwoven fabric decreases, the nonwoven fabric tends to soften.

When the thermoplastic resin contained in the fibers constituting the nonwoven fabric of the present embodiment comprises a polyolefin or is a polyolefin, the birefringence Δn of the fibers is preferably 0.015 or greater and 0.029 or less, more preferably 0.017 or greater and 0.027 or less, even more preferably 0.018 or greater and 0.026 or less, and particularly preferably 0.019 or greater and 0.025 or less. When the birefringence Δn is 0.015 or greater and 0.029 or less, crystallinity is low, and thus the amount of fatty acid amide migrating to the fiber surface is easily controlled. The measurement method for birefringence Δn will be described below.

The shape of the fiber constituting the nonwoven fabric of the present embodiment is not particularly limited. The fiber may be a core-sheath fiber or a crimped fiber. Further, the yarn cross-sectional shape may be a normal circular shape or an irregular cross-section.

The nonwoven fabric of the present embodiment contains a fatty acid amide in an amount of 0.01% by mass or greater and 1.5% by mass or less with respect to the total fiber mass. From the viewpoint of ease of migration from within the fibers to the fiber surface, specifically, from the viewpoint of obtaining a satisfactory effect of improving softness with a relatively small amount of fatty acid amide, the fatty acid amide preferably has a relatively low molecular weight. The number of carbon atoms in the fatty acid portion is preferably 24 or less, 22 or less, or 20 or less. From the viewpoint of not allowing an excessively large migration of fatty acid amide to the fiber surface to suppress slipperiness between nonwoven fabrics in a manufacturing process of products comprising the nonwoven fabric, the number of carbon atoms is preferably 12 or greater, 14 or greater, 16 or greater, or 18 or greater. Specific examples of a suitable fatty acid amide include lauramide, myristamide, palmitamide, stearamide, behenamide, oleamide, and erucamide. Erucamide is particularly preferable. A plurality of these fatty acid amides can be used in combination. The addition of a relatively small amount of fatty acid amide remarkably improves bending flexibility and slipperiness. If the content thereof is excessively high, slippage tends to occur in the manufacturing process of products (for example, sanitary materials) comprising the nonwoven fabric. From this viewpoint, the content percentage of the fatty acid amide with respect to the total fiber mass is appropriately 1.5% by mass or less, and is 0.01% by mass or greater, preferably 0.1% by mass or greater, more preferably 0.15% by mass or greater, and particularly preferably 0.2% by mass or greater in one aspect, and 1.5% by mass or less, preferably 1.0% by mass or less, and particularly preferably 0.6% by mass or less in one aspect.

The fatty acid amide coverage on the surface of the fibers constituting the nonwoven fabric of the present embodiment is 20% or greater and 90% or less, preferably 25% or greater and 80% or less, and more preferably 30% or greater and 70% or less. When the fatty acid amide coverage on the fiber surface is 20% or greater and 90% or less, control of slipperiness between nonwoven fabrics in the manufacturing process of products comprising the nonwoven fabric and sufficient softness can both be realized. The measurement method for fatty acid amide coverage on the fiber surface will be described below.

In the nonwoven fabric of the present embodiment, fibers may be bonded. Examples of the bonding method include a partial thermocompression bonding (point bonding) method, a hot-air method, a bonding method with a melted component (hot melt agent), and other methods. A partial thermocompression bonding method is preferable.

When the nonwoven fabric of the present embodiment is subjected to partial thermocompression bonding, the area ratio of partial thermocompression bonding portions (thermocompression bonding area ratio) with respect to the nonwoven fabric area, from the viewpoint of strength retention and softness, is preferably 3% or greater and 40% or less, more preferably 4% or greater and 25% or less, particularly preferably 4% or greater and 20% or less, and most preferably 5% or greater and 15% or less. In the present embodiment, as the partial thermocompression bonding area ratio decreases, the softening effect is exhibited more easily. Note that, the partial thermocompression bonding area ratio is a value measured by a method in which images of a nonwoven fabric enlarged with a microscope and photographed are analyzed.

The nonwoven fabric of the present embodiment may have a textured pattern obtained by a shaping process to obtain a satisfactory softness. Examples of the textured pattern include straight lines, curved lines, corners, circles, satin-like patterns, and other continuous or discontinuous patterns. To improve bending stiffness in both the machine direction (MD) and the cross-machine direction (CD), a carapace pattern is preferable. Further, from the viewpoint of softness, the depth of a recessed portion or a protruding portion (maximum difference between a recessed portion and a protruding portion) is preferably 0.1 mm or more and 5.0 mm or less, and even more preferably 0.2 mm or more and 3.0 mm or less. As the depth of the recessed or protruding portion increases, the effect increases. Further, the area ratio of recessed portions (pushed-in portions) of the texture with respect to the nonwoven fabric area, in order to obtain a satisfactory softness and feel, is preferably 5% or greater and 40% or less, and even more preferably 5% or greater and 25% or less. Note that, the maximum difference between a recessed portion and a protruding portion and the area ratio of recessed portions are values measured by a method in which images of the nonwoven fabric enlarged with a microscope and photographed are analyzed.

The basis weight of the nonwoven fabric of the present embodiment is preferably 8 g/m$^2$ or more and 40 g/m$^2$ or less, more preferably 10 g/m$^2$ or more and 30 g/m$^2$ or less, and particularly preferably 10 g/m$^2$ or more and 25 g/m$^2$ or less. When the basis weight is 8 g/m² or more, the nonwoven fabric has satisfactory strength that is particularly suitable for sanitary materials. When the basis weight is 40 g/m² or less, the nonwoven fabric is preferably imparted with excellent softness without giving the impression of a thick appearance.

The nonwoven fabric of the present embodiment may contain a hydrophilizing agent. As the hydrophilizing agent, a nonionic surfactant in which ethylene oxide is added to a higher alcohol, a higher fatty acid, or alkylphenol; or an anionic surfactant such as an alkyl phosphate salt or an alkyl sulfate salt is preferably used alone or in a mixture, in consideration of safety to the human body and process safety.

The content of the hydrophilizing agent varies depending on the required performance of the nonwoven fabric. Normally, the content thereof with respect to 100 parts by mass of the fibers is preferably within the range of 0.1 parts by mass or more and 1.0 parts by mass or less, more preferably 0.15 parts by mass or more and 0.8 parts by mass or less, and even more preferably 0.2 parts by mass or more and 0.6 parts by mass or less. When the content of the hydrophilizing agent is 0.1 parts by mass or more and 1.0 parts by mass or less, the nonwoven fabric can be imparted with excellent hydrophilic performance and processability, which is particularly preferable for topsheets of sanitary materials.

The nonwoven fabric of the present embodiment may be further blended with a nucleating agent, a flame retardant, an inorganic filler, a pigment, a colorant, a heat-resistant stabilizer, or an antistatic agent.

By controlling the average single yarn fineness of the fibers and the existing state of fatty acid amide within the fibers and on the fiber surface, the nonwoven fabric of the present embodiment can be imparted with both a reduced slipperiness and a satisfactory softness.

In one aspect, the slip length of the nonwoven fabric can preferably be 40 mm or less, 35 mm or less, or 30 mm or less. When the slip length is 40 mm or less, slippage in a manufacturing process of products (for example, sanitary materials) comprising the nonwoven fabric does not easily occur. In one aspect, from the viewpoint of softness of the nonwoven fabric, the slip length can be 8 mm or more, 10 mm or more, or 12 mm or more. The measurement method for slip length will be described below.

In one aspect, the bending stiffness of the nonwoven fabric can preferably be 50 mm or less, 45 mm or less, or 40 mm or less. When the bending stiffness is 50 mm or less, a comfortable texture suitable to the touch as a nonwoven fabric particularly for sanitary materials is obtained. In one aspect, from the viewpoint of ease of manufacture of the nonwoven fabric, the bending stiffness can be 10 mm or more, 15 mm or more, and 20 mm or more. The measurement method for bending stiffness will be described below.

In the nonwoven fabric of the present embodiment, the fatty acid amide coverage on the fiber surface is set to a specific range, whereby satisfactory sealing property can be shown. In one aspect, the peel strength of a sealing portion when two sheets of the nonwoven fabric of the present embodiment are stacked and then laminated by a thermal bonding method using a heat sealer at a temperature of 150° C. and a pressure of 1.4 MPa can preferably be 0.5 N/5 cm or more, 0.7 N/5 cm or more, and 1.0 N/5 cm or more. When the above peel strength is 0.5 N/5 cm or more, a strength particularly suitable for absorbent articles can be obtained. In one aspect, from the viewpoint of ease of manufacture of the nonwoven fabric, the above peel strength may be 25 N/5 cm or less, 23 N/5 cm or less, or 21 N/5 cm or less. The details of the measurement method for peel strength will be described below. In an aspect of the present invention, a nonwoven fabric including a sealing portion which has a peel strength within the above range is also provided. Note that, the sealing portion of the nonwoven fabric of the present embodiment can be formed according to a bonding method with a melted component (hot melt agent), a thermal bonding method, an ultrasonic method, or another method.

The tensile strength of the nonwoven fabric of the present embodiment, as an average value of the machine direction and the cross-machine direction, is preferably 13 N/3 cm or more, more preferably 13.5 N/3 cm or more and 21 N/3 cm or less, and even more preferably 14 N/3 cm or more and 20 N/3 cm or less. When the tensile strength is 13 N/3 cm or more, the nonwoven fabric does not easily rupture, which is preferable when used for sanitary materials.

The 5% elongation stress of the nonwoven fabric of the present embodiment, as an average value of the machine direction and the cross-machine direction, is preferably 7 N/3 cm or less, more preferably 3 N/3 cm or more and 6.5 N/3 cm or less, and even more preferably 4 N/3 cm or more and 6.5 N/3 cm or less. When the 5% elongation stress is 7 N/3 cm or less, good texture and excellent softness particularly for a nonwoven fabric in sanitary materials are obtained.

<Method for Manufacturing Nonwoven Fabric>

An aspect of the present invention also provides a method for manufacturing a nonwoven fabric. The method for manufacturing the nonwoven fabric of the present embodiment is not particularly limited, but is preferably a spunbond method. The spunbond method generally comprises a spinning step, a cooling step, a collection step, and a bonding step. In the spinning step, a melted raw material resin is discharged from a nozzle. In the cooling step, the resin discharged in the spinning step is cooled by cold air to form a filamentous material. In the collection step, the filamentous material is collected on a moving collection surface to form a web. In a bonding step, the web is bonded by partial thermocompression bonding. The spunbond method may comprise a stretching step between the cooling step and the collection step, in which a high-speed airflow drawing apparatus is used to stretch (draw) the filamentous material by air jet.

In the spinning step, a discharge rate determined by the following formula:

$$\text{Discharge rate (m/min)} = \text{single-hole discharge amount (g/min)} / \{\text{melt density (g/cm}^3) \times [\text{single-hole diameter (mm)}/2]^2 \times \pi\}$$

is preferably 1 m/min or more and 15 m/min or less, more preferably 3 m/min or more and 10 m/min or less, and particularly preferably 4 m/min or more and 8 m/min or less. When the discharge rate is 1 m/min or more, excessive migration of the fatty acid amide to the fiber surface is easily inhibited, and a nonwoven fabric having an advantageous strength particularly for sanitary material applications can be obtained. When the discharge rate is 15 m/min or less, spinning can be stably carried out without yarn breakage.

In the spinning step, the temperature of the spinneret is preferably 200° C. or higher and 300° C. or lower, more preferably 210° C. or higher and 280° C. or lower, and particularly preferably 220° C. or higher and 260° C. or lower. When the temperature of the spinneret is set to 200° C. or higher and 300° C. or less to spin at a relatively low temperature, since excess heat is not applied to the thermoplastic resin, excessive migration of the fatty acid amide to the fiber surface is easily inhibited. Moreover, when a resin having a relatively high MFR (for example, MFR at 230° C. is 5 g/10 min or more) is used as the thermoplastic resin, stable spinning can preferably be carried out even at a low spinning temperature.

In the cooling step, the cold air speed is preferably 0.4 m/s or more and 2.0 m/s or less, and more preferably 0.5 m/s or more and 1.5 m/s or less. By setting the cold air speed to 0.4 m/s or more for rapid cooling, crystallinity of the fibers is controlled (more specifically, crystallinity is lowered), and excessive migration of the fatty acid amide to the fiber surface is easily inhibited.

In the bonding step, the web collected on the moving collection surface in the collection step is preferably integrated on both sides by bonding. Examples of the bonding method include a partial thermocompression bonding (point bonding) method, a hot-air method, a bonding method with a melted component (hot melt agent), and other methods, but a partial thermocompression bonding is preferable. In the manufacture of the nonwoven fabric of the present embodiment, the partial thermocompression bonding can be carried out by an ultrasonic method or by passing the web through heated embossing rolls, whereby both sides are integrated and a raised and sunken pattern of, for example, pinpoint shapes, elliptical shapes, diamond shapes, rectangular shapes, or diagonal splash shapes is distributed on the entire surface of the nonwoven fabric. From the viewpoint of productivity, it is preferable that heated embossing rolls are used in the partial thermocompression bonding. Note that, the fatty acid amide and the low-melting-temperature thermoplastic resin have the effect of lowering compression bonding temperature of the nonwoven fabric and can mitigate a hardening phenomenon in the nonwoven fabric caused by film formation accompanying the thermocompression bonding. The method of incorporating the fatty acid amide and the low-melting-point thermoplastic resin into the fibers is preferably a polymer blending method which facilitates uniform mixing in the fibers.

When a hydrophilizing agent is applied to the nonwoven fabric of the present embodiment, normally, a diluted hydrophilizing agent is used and a known method, such as an immersion method, a spraying method, or a coating (kiss coater or gravure coater) method, can be adopted as the application method. If necessary, a premixed hydrophilizing agent is preferably diluted with a solvent such as water before application.

When a hydrophilizing agent is diluted with a solvent such as water and applied, a drying step may be necessary. In that case, a known method using convective heat transfer, conductive heat transfer, or radiative heat transfer can be adopted as the drying method. A method of drying by hot air or infrared rays or drying by heat contact can be used.

<Absorbent Article>

An absorbent article comprising the nonwoven fabric described above is also an aspect of the present invention. In one aspect, the absorbent article is a sanitary material for absorbing urine and splashed liquids. The nonwoven fabric of the present invention includes a texture comfortable to the touch, and is thus preferably used in absorbent articles worn on the human body. Specific examples of the absorbent article of the present invention include disposable diapers, sanitary napkins, and incontinence pads.

EXAMPLES

Hereinafter, the present invention will be specifically described with reference to the Examples and Comparative Examples. However, the present invention is not limited only to the Examples below. Additionally, the evaluation method for each property is as described below.

1. Average Single Yarn Fineness (Dtex)

Excluding 10 cm on both ends in the width direction, a nonwoven fabric was divided into five substantially equal parts in the width direction to obtain sample test pieces of 1 cm squares. The diameter of each fiber was measured at 20 points with an optical microscope (manufactured by Keyence Corporation: VHX-8000). From an average value thereof, fineness was calculated.

2. Basis Weight (g/m$^2$)

In accordance with JIS-L1906, five test pieces having a length of 20 cm by a width of 5 cm were arbitrarily taken from a nonwoven fabric and weighed. From an average value thereof, a weight per unit area was calculated.

3. MFR (g/10 min)

Using a melt indexer (manufactured by Toyo Seiki Co., Ltd.: MELT INDEXER S-101) melt flow apparatus, a melted polymer discharge amount (g) per 10 min was calculated from the time required to discharge a certain volume of thermoplastic resin under the conditions of an orifice diameter of 2.095 mm, an orifice length of 0.8 mm, a load of 2160 g, and a measurement temperature of 230° C.

4. Melting Point Measurement (DSC)

The melting point was measured using a differential scanning calorimeter (DSC) (manufactured by Perkin-Elmer Corporation: DSC6000). 3 mg of thermoplastic resin was used as a measurement sample. The thermoplastic resin was spread over an aluminum open sample pan having a diameter of 5 mm, and a clamping cover was placed on and fixed in the aluminum pan with a sample sealer. The temperature was measured from 30° C. to 300° C. in a nitrogen atmosphere at a temperature elevation rate of 10° C./min, and the temperature at which the melting endothermic curve reached the maximum was taken as the melting point.

5. Discharge Rate

The discharge rate was calculated from the following formula.

$$\text{Discharge rate (m/min)} = \text{single-hole discharge amount (g/min)} / \{\text{melt density (g/cm}^3) \times [\text{single-hole diameter (cm)}/2]^2 \times \pi\}$$

Additionally, the melt density was calculated from the following formula, using a melt indexer (manufactured by Toyo Seiki Co., Ltd.: MELT INDEXER S-101) melt flow apparatus.

$$\text{Melt density (g/cm}^3) = \text{weight of extrudate (g)} / \{\text{cross-sectional area of orifice (cm}^2) \times \text{piston travel distance (cm)}\}$$

6. Fatty Acid Amide Coverage (%)

10 fibers were sampled from a nonwoven fabric, coated with osmium, and observed morphologically using a field emission scanning electron microscope (FE-SEM) (manufactured by Hitachi High-Tech Corporation: SU8220) at an acceleration voltage of 0.8 kV. The SEM image was binarized. For each of the 10 fibers, the area ratio of deposits on the fiber surface with respect to the entire fiber was measured. An average of the 10 fibers was calculated as the fatty acid amide coverage.

7. Birefringence Δn

The birefringence of the nonwoven fabric was measured by interference fringe method using a transmission quantitative interference microscope (interference microscope Interphako manufactured by Carl Zeiss Jena). 10 points were measured, and an average value of the birefringence of the 10 points was calculated as the birefringence Δn.

8. Slip Length (Mm) (Slipperiness in Sanitary Material Manufacturing Process)

A nonwoven fabric adhered to the bottom surface of a weight having a length of 20 cm, a width of 10 cm, a height of 2 cm, and a weight of 100 g, which was assumed to be a sanitary material, was placed on another nonwoven fabric adhered to a flat table so as to be in contact with each other. The travel distance of the weight when a force of 3 N was applied to a side surface of the weight for 0.1 s was measured. Five points on each of the front and back sides and in the machine and cross-machine directions, totaling 20 points, were measured, and the measurement values were averaged, whereby a slip length (mm) was calculated. A smaller slip length (mm) value indicates that slippage is less likely to occur in a sanitary material manufacturing process.

9. Bending Stiffness (Mm) (Softness)

The bending stiffness was measured in accordance with the 45° cantilever method of JIS-L1096. Five test pieces having a width of 20 mm and a length of 150 mm were arbitrarily taken in each of the machine and cross-machine directions from a nonwoven fabric sample. A test piece was placed on a smooth cross-machine table having a surface with a 45° slope at one end, and a short side thereof was aligned with the scale baseline. The test piece was then carefully slid in the direction of the slope. When the center point of one end of the test piece comes in contact with the slope, the position of the other end was measured with the scale. The length (mm) traveled by the test piece was measured on the front and back sides for each of the five test pieces, and the values were averaged to obtain a bending stiffness.

10. Sealing Portion Peel Strength (N/5 cm)

Test pieces having a width of 5 cm and a length of 20 cm were arbitrarily taken in the machine and cross-machine directions from a nonwoven fabric. Two of the nonwoven fabrics were laminated to each other on the embossed surfaces. Using a heat sealer having a bonding width of 7 mm at a position 3 cm from the end of one short side, thermocompression bonding was carried out at a temperature of 150° C. and a pressure of 1.4 MPa across the entire width perpendicular to the length direction of a test piece. Each of the two nonwoven fabrics was clamped at a clamping interval of 5 cm in a tensile tester, so that the thermocompression-bonded portion was in the center. Tensile testing was carried out so as to peel off the thermocompression-bonded portion at a tensile speed of 30 cm/min, and the breaking strength was measured. Samples were measured at five point each in the machine and cross-machine directions, and the values were averaged to calculate a breaking strength in the machine direction and a breaking strength in the cross-machine direction. These values were then averaged to obtain the peel strength of the sealing portion.

Example 1

To a polypropylene resin having an MFR of 55 g/10 min (measured at a temperature of 230° C. and a load of 2.16 kg in accordance with JIS-K7210) and a melting point of 160° C., there were added erucamide as the fatty acid amide, in an amount which makes an intra-fiber content percentage of 0.4% by mass, and a polypropylene-based elastomer having an MFR of 20 g/10 min and a melting point of 80° C. as the low-melting-point thermoplastic resin, in an amount which makes an intra-fiber content percentage of 5% by mass. The resulting mixture was extruded from a spin nozzle having a nozzle diameter of 0.4 mm at a single-hole discharge amount of 0.5 g/min·hole, a spinning temperature of 230° C., and a discharge rate of 5.2 m/min. The discharged yarn was cooled with cold air at a wind speed of 0.7 m/s, then drawn using a high-speed airflow drawing apparatus by air jet, and collected on a moving collection surface to obtain a web. Subsequently, the resulting web was passed between a flat roll and an embossing roll (pattern specification: diameter of 0.5 mm, staggered array, traverse pitch of 2 mm, longitudinal pitch of 2 mm, and compression bonding area ratio of 6.3%), whereby fibers were bonded at a temperature of 136° C. and linear pressure of 35 kN/m to obtain a filament nonwoven fabric having a basis weight of 15 g/m². The physical properties of the resulting filament nonwoven fabric are shown in Table 1.

Example 2

Except that the content percentage of the fatty acid amide was set to 0.5% by mass and the content percentage of the low-melting-point thermoplastic resin was set to 10% by mass, a filament nonwoven fabric was obtained in the same manner as in Example 1. The physical properties of the resulting filament nonwoven fabric are shown in Table 1.

Example 3

Except that the content percentage of the fatty acid amide was set to 0.7% by mass, the content percentage of the low-melting-point thermoplastic resin was set to 0% by mass, and the speed of the moving collection surface was adjusted so as to provide a basis weight of 17 g/m², a filament nonwoven fabric was obtained in the same manner as in Example 1. The physical properties of the resulting filament nonwoven fabric are shown in Table 1.

Example 4

Except that the content percentage of the fatty acid amide was set to 1.0% by mass, a filament nonwoven fabric was obtained in the same manner as in Example 3. The physical properties of the resulting filament nonwoven fabric are shown in Table 1.

Example 5

Except that a polypropylene resin having an MFR of 35 g/10 min (measured at a temperature of 230° C. and a load of 2.16 kg in accordance with JIS-K7210) was used, and the content percentage of the fatty acid amide was set to 0.8% by mass, the content percentage of the low-melting-point thermoplastic resin to 4% by mass, and the spinning temperature to 250° C., a filament nonwoven fabric was obtained in the same manner as in Example 1. The physical properties of the resulting filament nonwoven fabric are shown in Table 1.

Example 6

Except that the content percentage of the fatty acid amide was set to 0.3% by mass, the content percentage of the low-melting-point thermoplastic resin was set to 3% by mass, and the speed of the moving collection surface was adjusted so as to provide a basis weight of 17 g/m², a filament nonwoven fabric was obtained in the same manner as in Example 5. The physical properties of the resulting filament nonwoven fabric are shown in Table 1.

Example 7

Except that the content percentage of the low-melting-point thermoplastic resin was set to 2% by mass, a filament nonwoven fabric was obtained in the same manner as in Example 3. The physical properties of the resulting filament nonwoven fabric are shown in Table 1.

Example 8

Except that the content percentage of the fatty acid amide was set to 0.6% by mass and the content percentage of the low-melting-point thermoplastic resin was set to 1% by mass, a filament nonwoven fabric was obtained in the same manner as in Example 3.

Example 9

Except that a polyethylene resin having an MFR of 33 g/10 min (measured at a temperature of 230° C. and a load of 2.16 kg in accordance with JIS-K7210) and a melting point of 120° C. was used, and the content percentage of the fatty acid amide was set to 0.3% by mass, the content percentage of the low-melting-point thermoplastic resin to 5% by mass, and the spinning temperature to 240° C., a filament nonwoven fabric was obtained in the same manner as in Example 3. The physical properties of the resulting filament nonwoven fabric are shown in Table 1.

Example 10

Except that an extrudate of a mixture of a polypropylene resin having an MFR of 35 g/10 min (measured at a temperature of 230° C. and a load of 2.16 kg in accordance with JIS-K7210) and a melting point of 160° C., a fatty acid amide, and a low-melting-point thermoplastic resin was used as the core component and an extrudate of a mixture of a polyethylene resin having an MFR of 35 g/10 min (measured at a temperature of 230° C. and a load of 2.16 kg in accordance with JIS-K7210) and a melting point of 120° C., a fatty acid amide, and a low-melting-point thermoplastic resin was used as the sheath component to form a sheath-core structure having a component ratio of 50/50 (mass ratio), and the content percentage of the fatty acid amide was set to 0.4% by mass in both sheath and core, the content percentage of the low-melting-point thermoplastic resin to 5% by mass in both sheath and core, and the spinning temperature to 240° C., a filament nonwoven fabric was obtained in the same manner as in Example 3. The physical properties of the resulting filament nonwoven fabric are shown in Table 1.

Example 11

Except that the content percentage of the fatty acid amide was set to 0.1% by mass and the content percentage of the low-melting-point thermoplastic resin was set to 8% by mass, a filament nonwoven fabric was obtained in the same manner as in Example 3. The physical properties of the resulting filament nonwoven fabric are shown in Table 1.

Example 12

Except that the content percentage of the fatty acid amide was set to 0.2% by mass and the content percentage of the low-melting-point thermoplastic resin was set to 15% by mass, a filament nonwoven fabric was obtained in the same manner as in Example 3. The physical properties of the resulting filament nonwoven fabric are shown in Table 1.

Example 13

Except that stearamide was used as the fatty acid amide, a filament nonwoven fabric was obtained in the same manner as in Example 1. The physical properties of the resulting filament nonwoven fabric are shown in Table 1.

Example 14

Except that oleamide was used as the fatty acid amide, a filament nonwoven fabric was obtained in the same manner as in Example 1. The physical properties of the resulting filament nonwoven fabric are shown in Table 1.

Example 15

Except that ethylene bis stearamide was used as the fatty acid amide, a filament nonwoven fabric was obtained in the same manner as in Example 1. The physical properties of the resulting filament nonwoven fabric are shown in Table 1.

Comparative Example 1

Except that the content percentage of the fatty acid amide was set to 0.005% by mass and the content percentage of the low-melting-point thermoplastic resin was set to 5% by mass, a filament nonwoven fabric was obtained in the same manner as in Example 3. The physical properties of the resulting filament nonwoven fabric are shown in Table 1.

Comparative Example 2

Except that the content percentage of the fatty acid amide was set to 2.0% by mass and the content percentage of the low-melting-point thermoplastic resin was set to 5% by mass, a filament nonwoven fabric was obtained in the same manner as in Example 3. The physical properties of the resulting filament nonwoven fabric are shown in Table 1.

Comparative Example 3

Except that the content percentage of the fatty acid amide was set to 0% by mass and the content percentage of the low-melting-point thermoplastic resin was set to 5% by mass, a filament nonwoven fabric was obtained in the same manner as in Example 3. The physical properties of the resulting filament nonwoven fabric are shown in Table 1.

Comparative Example 4

Except that the content percentage of the fatty acid amide was set to 0.5% by mass, the content percentage of the low-melting-point thermoplastic resin was set to 10% by mass, extrusion was carried out at a single-hole discharge amount of 0.8 g/min·hole, a spinning temperature of 250° C., and a discharge rate of 33.6 m/min from a spin nozzle having a nozzle diameter of 0.2 mm, the discharged yarn was cooled with cold air at a wind speed of 0.3 m/s, and the drawing force by air jet was set to 1.7 times, a filament nonwoven fabric was obtained in the same manner as in Example 3. The physical properties of the resulting filament nonwoven fabric are shown in Table 1.

Comparative Example 5

Except that extrusion was carried out at a single-hole discharge amount of 0.5 g/min·hole and a discharge rate of 0.9 m/min from a spin nozzle having a nozzle diameter of 0.95 mm, a filament nonwoven fabric was obtained in the same manner as in Example 1. The physical properties of the resulting filament nonwoven fabric are shown in Table 1.

Comparative Example 6

Except that cooling was carried out with cold air having a wind speed of 2.1 m/s, a filament nonwoven fabric was obtained in the same manner as in Example 1. The physical properties of the resulting filament nonwoven fabric are shown in Table 1.

TABLE 1

| | Unit | Example 1 | Example 2 | Example 3 | Example 4 | Example 5 | Example 6 | Example 7 | Example 8 |
|---|---|---|---|---|---|---|---|---|---|
| Type of thermoplastic resin | — | PP | PP | PP | PP | PP | PP | PP | PP |
| Melting point of thermoplastic resin | °C. | 160 | 160 | 160 | 160 | 160 | 160 | 160 | 160 |
| Spinning temperature | °C. | 230 | 230 | 230 | 230 | 250 | 250 | 230 | 230 |
| Discharge rate | m/min | 5.2 | 5.2 | 5.2 | 5.2 | 5.2 | 5.2 | 5.2 | 5.2 |
| Cold air wind speed | m/s | 0.7 | 0.7 | 0.7 | 0.7 | 0.7 | 0.7 | 0.7 | 0.7 |
| Average single yarn fineness | dtex | 1.5 | 1.6 | 1.5 | 1.7 | 1.5 | 1.7 | 1.7 | 1.7 |
| Birefringence Δn | — | 0.024 | 0.023 | 0.025 | 0.022 | 0.024 | 0.021 | 0.022 | 0.023 |
| Basis weight | g/m² | 15 | 15 | 17 | 17 | 15 | 17 | 17 | 17 |
| Type of fatty acid amide | — | Erucamide | Erucamide | Erucamide | Erucamide | Erucamide | Erucamide | Erucamide | Erucamide |
| Fatty acid amide content percentage | % by mass | 0.4 | 0.5 | 0.7 | 1.0 | 0.8 | 0.3 | 0.7 | 0.6 |
| Low-melting-point thermoplastic resin content percentage | % by mass | 5 | 10 | 0 | 0 | 4 | 3 | 2 | 1 |
| Fatty acid amide coverage | % | 63 | 72 | 41 | 56 | 67 | 43 | 73 | 54 |
| Bending stiffness | mm | 37 | 32 | 46 | 42 | 35 | 41 | 35 | 39 |
| Peel strength of sealing portion | N/5 cm | 0.8 | 0.7 | 1.0 | 0.8 | 0.7 | 0.8 | 0.7 | 0.7 |
| Slip length | mm | 25 | 31 | 20 | 28 | 36 | 21 | 37 | 26 |

| | Unit | Example 9 | Example 10 | Example 11 | Example 12 | Example 13 | Example 14 | Example 15 |
|---|---|---|---|---|---|---|---|---|
| Type of thermoplastic resin | — | PE | PE/PP | PP | PP | PP | PP | PP |
| Melting point of thermoplastic resin | °C. | 120 | 120/160 | 160 | 160 | 160 | 160 | 160 |
| Spinning temperature | °C. | 240 | 240 | 230 | 230 | 230 | 230 | 230 |
| Discharge rate | m/min | 5.2 | 5.2 | 5.2 | 5.2 | 5.2 | 5.2 | 5.2 |
| Cold air wind speed | m/s | 0.7 | 0.7 | 0.7 | 0.7 | 0.7 | 0.7 | 0.7 |
| Average single yarn fineness | dtex | 2.0 | 2.0 | 1.7 | 1.7 | 1.5 | 1.5 | 1.5 |
| Birefringence Δn | — | 0.019 | 0.020 | 0.023 | 0.024 | 0.024 | 0.024 | 0.024 |
| Basis weight | g/m² | 17 | 17 | 17 | 17 | 15 | 15 | 15 |
| Type of fatty acid amide | — | Erucamide | Erucamide | Erucamide | Erucamide | Stearamide | Oleamide | Ethylene bis stearamide |
| Fatty acid amide content percentage | % by mass | 0.3 | 0.4 | 0.1 | 0.2 | 0.4 | 0.4 | 0.4 |
| Low-melting-point thermoplastic resin content percentage | % by mass | 5 | 5 | 8 | 15 | 5 | 5 | 5 |
| Fatty acid amide coverage | % | 56 | 62 | 21 | 28 | 72 | 74 | 51 |
| Bending stiffness | mm | 27 | 32 | 38 | 33 | 37 | 37 | 37 |
| Peel strength of sealing portion | N/5 cm | 0.5 | 0.6 | 0.9 | 0.7 | 0.7 | 0.7 | 0.8 |
| Slip length | mm | 33 | 32 | 17 | 19 | 35 | 35 | 23 |

| | Unit | Comparative Example 1 | Comparative Example 2 | Comparative Example 3 | Comparative Example 4 | Comparative Example 5 | Comparative Example 6 |
|---|---|---|---|---|---|---|---|
| Type of thermoplastic resin | — | PP | PP | PP | PP | PP | PP |
| Melting point of thermoplastic resin | °C. | 160 | 160 | 160 | 160 | 160 | 160 |
| Spinning temperature | °C. | 230 | 230 | 230 | 230 | 230 | 230 |
| Discharge rate | m/min | 5.2 | 5.2 | 5.2 | 33.6 | 0.9 | 5.2 |
| Cold air wind speed | m/s | 0.7 | 0.7 | 0.7 | 0.7 | 0.7 | 2.1 |
| Average single yarn fineness | dtex | 1.4 | 1.4 | 1.5 | 1.5 | 1.5 | 1.5 |
| Birefringence Δn | — | 0.023 | 0.022 | 0.021 | 0.030 | 0.030 | 0.014 |
| Basis weight | g/m² | 17 | 17 | 17 | 17 | 17 | 17 |

TABLE 1-continued

|  |  |  |  |  |  |  |  |
|---|---|---|---|---|---|---|---|
| Type of fatty acid amide | — | — | Erucamide | Erucamide | Erucamide | Erucamide | Erucamide | Erucamide |
| Fatty acid amide content percentage | % by mass | 0.005 | 2.0 | 0 | 0.5 | 0.4 | 0.4 |
| Low-melting-point thermoplastic resin content percentage | % by mass | 5 | 5 | 5 | 10 | 5 | 5 |
| Fatty acid amide coverage | % | 4 | 94 | 0 | 91 | 91 | 18 |
| Bending stiffness | mm | 55 | 42 | 57 | 35 | 35 | 52 |
| Peel strength of sealing portion | N/5 cm | 0.8 | 0.5 | 0.8 | 0.5 | 0.5 | 0.8 |
| Slip length | mm | 12 | 52 | 11 | 48 | 47 | 16 |

INDUSTRIAL APPLICABILITY

The nonwoven fabric provided by the present invention is capable of imparting a sense of sufficient softness when touched by human hands while suppressing slipperiness between nonwoven fabrics in a manufacturing process of products (for example, sanitary materials) comprising the nonwoven fabric, and thus can be suitably used for absorbent articles such as sanitary materials, for example, topsheets, backsheets, and side gathers of disposable diapers.

The invention claimed is:

1. A nonwoven fabric comprised of fibers comprising a thermoplastic resin, wherein an average yarn single fineness of the fibers is 0.7 dtex or more and 4.0 dtex or less, the fibers contain a fatty acid amide in an amount of 0.01% by mass or greater and 1.5% by mass or less with respect to a total fiber mass, and a fatty acid amide coverage on a surface of the fibers is 20% or greater and 90% or less, wherein the thermoplastic resin is a polyolefin and a birefringence Δn of the fibers is 0.015 or greater and 0.029 or less.

2. The nonwoven fabric according to claim 1, wherein the fibers contain a fatty acid amide in an amount of 0.6% by mass or less with respect to the total fiber mass.

3. The nonwoven fabric according to claim 1, wherein the fibers contain a fatty acid amide in an amount of 0.1% by mass or greater with respect to the total fiber mass.

4. The nonwoven fabric according to claim 1, wherein a fatty acid portion of the fatty acid amide has 22 carbon atoms or less.

5. The nonwoven fabric according to claim 1, wherein the fatty acid amide is erucamide.

6. The nonwoven fabric according to claim 1, wherein the thermoplastic resin contains 70% by mass or greater and 99% by mass or less of a high-melting-point thermoplastic resin having a melting point above a predetermined melting point and contains 1% by mass or more and 30% by mass or less of a low-melting-point thermoplastic resin having a melting point below or equal to the predetermined melting point, wherein the predetermined melting point is 110° C.

7. The nonwoven fabric according to claim 1 which is a filament nonwoven fabric.

8. An absorbent article comprising the nonwoven fabric according to claim 1.

9. The absorbent article according to claim 8 which is a disposable diaper, a sanitary napkin, or an incontinence pad.

10. A manufacturing method for the nonwoven fabric according to claim 1, wherein
the method is a spunbond method comprising a spinning step, a cooling step, a collection step, and a bonding step,
a discharge rate in the spinning step is 4 m/min or more and 8 m/min or less, and
a cold air speed in the cooling step is 0.5 m/s or more and 1.5 m/s or less.

11. The manufacturing method for a nonwoven fabric according to claim 10, wherein the fatty acid amide is erucamide.

* * * * *